United States Patent

Cucinella et al.

[11] 4,022,809
[45] May 10, 1977

[54] PROCESS FOR THE PREPARATION OF POLY-N-ALKYLIMINOALANES

[75] Inventors: Salvatore Cucinella, San Donato Milanese; Giovanni Dozzi, Milano Alessandro Mazzei, San Donato Milanese, all of Italy

[73] Assignee: Snam Progetti S.p.A., Milano, Italy

[22] Filed: Nov. 15, 1974

[21] Appl. No.: 524,312

[30] Foreign Application Priority Data

Nov. 29, 1973 Italy ............................... 31857/73

[52] U.S. Cl. ........................... 260/448 R; 260/2 M
[51] Int. Cl.² .......................................... C07F 5/06
[58] Field of Search ...................... 260/448 R, 2 M

[56] References Cited
UNITED STATES PATENTS 3,255,169   6/1966   Kearby ...................... 260/448 R X

OTHER PUBLICATIONS

Ehrlich et al., Inorganic Chemistry, vol. 3, No. 5, pp. 628–631 (1964).
Gerrard, Trans. J. Plastics Inst., Inorganic Polymers, pp. 509, 520, 522, 523 (1967).

*Primary Examiner*—Helen M. S. Sneed
*Attorney, Agent, or Firm*—Ralph M. Watson

[57] ABSTRACT

A poly-N-alkyliminoalane containing repeated imine units of the type

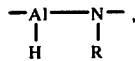

wherein R is an aliphatic radical, is prepared by reacting an alane of an alkali or alkali-earth metal with a primary amine in the presence of a hydrocarbon solvent.

5 Claims, No Drawings

PROCESS FOR THE PREPARATION OF POLY-N-ALKYLIMINOALANES

The present invention relates to a process, which is very advantageous from a technical and economical point of view, for the preparation of poly-N-alkyliminoalanes, i.e. compounds which are characterized by the presence of imine units of the type –Al–H–NR– bound to one another to form structures $[AlH-NR]_n$ wherein $n$ means the association degree and R may be an aliphatic, cycloaliphatic or aromatic radical.

It is known that poly-N-alkyliminoalanes, hereinafter referred to more simply as PIA, may be utilized as active co-catalysts in the synthesis of polyethylene and highly stereospecific olefinic and diolefinic polymers as well as in the reduction of organic derivatives with an asymmetrical induction: the results obtained render these compounds very important from an industrial point of view.

It is also known that PIA can be synthetized through many methods starting from complexes of $AlH_3$ with Lewis bases, alkali metal alanates and aluminum triamides according to the matter disclosed in "Die Makromoleculare Chemie 122, (1969) pages 168–185."

All of the aforesaid methods necessitate filtration of the reaction by-products constituted by the alkali metal halides and/or the employment of various solvents which further make it necessary to carry out separation processes.

Particularly, when use is made of complexes formed by aluminum hydride and Lewis bases, let us emphasize that these are obtained by reacting $MAlH_4$ (M is an alkali metal) or $M'(AlH_4)_2$ (M' is an alkali-earth metal) with aluminum halides, particularly $AlCl_3$, according to a total reaction, which gives rise to PIA, as follows $$3\ MAlH_4 + AlCl_3 \xrightarrow{ether} 3MCl + 4AlH_3 \quad (1a)$$

$$AlH_3 + R-NH_2 \rightarrow 2H_2 + PIA \quad (1b)$$

halide which is formed at the expense of one atom of hydride hydrogen as in the following scheme $$Li\ AlH_4 + HCl \cdot H_2NR_2$$
$$LiCl + [AlH_3 \cdot RNH_2] + H_2$$

$$[AlH_3 \cdot R\ NH_2] \rightarrow PIA + 2H_2$$

It has now been found, which is the subject of the present invention, that PIA can be synthetized through a novel process, which eliminates all the drawbacks above listed for the methods known till now.

According to the present invention it is possible to prepare poly-N-alkyliminoalanes by directly reacting alkali or alkali-earth metal alanates with primary amines in the presence of a hydrocarbon solvent.

The reaction, in the case of alkali metal alanates, can be schematized as follows $$MAlH_4 + RNH_2 \rightarrow MH + PIA + 2H_2$$

and presents the following advantages with respect to the known methods
 a. it does not involve the formation and subsequent filtration of alkali metal or alkaline-earth metal halides;
 b. it does not involve the loss of hydride hydrogen corresponding to the formation of alkali metal or alkaline-earth metal halide as from (a);
 c. it takes place directly in a hydrocarbon solvent without any polar solvent, making it possible to eliminate the use of different solvents in the various stages of the reaction and the associated problems of replacement and separation for recycle;
 d. it allows the recovery of the alkali or alkali-earth metal hydride, which may be again employed for the synthesis of $MAlH_4$ through a direct reaction of MH with aluminum and hydrogen by known methods.

The advantage of the process can be better understood by considering the following total scheme $$MalH_4 + H_2NR \rightarrow \frac{1}{N}(AlHNR)_n + MH + 2H_2; MH + Al + \frac{3}{2}H_2 \rightarrow MAlH_4$$

---

$$Al + \frac{2}{3}H_2 + H_2NR \rightarrow \frac{1}{n}(AlHNR)_n + 2H_2$$

The reaction 1a occurs in the presence of polar solvents, for instance ethyl ether. Therefore, when hydrocarbon solutions are desired free from traces of polar substances, as required in the employment of PIA as polymerization cocatalyst, it is necessary to perform, in addition to the filtration of MCl, the complete removal of the polar solvent from the final reaction product and the replacement thereof with the wished solvent.

It is indeed true that the employment of various solvents might be avoided by employing hydrocarbon solutions of $AlH_3 \cdot NR_3$ (obtainable by reacting $LiAlH_4$ with $NR_3 \cdot HCl$).

However the problem of the expensive removal of $NR_3$ from the PIA hydrocarbon solution would then exist.

Also the methods, which directly use lithium aluminum hydride and $R-NH_2 \cdot HCl$ as starting products in PIA formation, require the filtration of the alkali metal whose convenience, also from an economical point of view, is evident since it is possible to achieve the synthesis of PIA by employing $Al, H_2$ and amine.

In the practice of our invention it is possible to employ any alkali or alkali-earth metal; however an advantageous use has been emphasized for $LiAlH_4$, $NaAlH$, $Li_3AlH_6$ and $Na_3\ AlH_6$ whereas the amine is selected from the primary aliphatic, cycloaliphatic or aromatic amines.

The reaction, as noted above, occurs in the presence of a hydrocarbon solvent, selected from the aliphatic, cycloaliphatic and aromatic hydrocarbons, at temperatures ranging from $-20°$ to $+250°$ C, preferably at a temperature ranging from room temperature to $150°$ C.

The reaction pressure is not very important for a good running thereof; we prefer to operate at atmospheric pressure or at a pressure equal to the solvent vapour pressure.

EXAMPLE 1

A solution of 15.7 ml of iso $C_3H_7 - NH_2$ (185 mmoles) in 30 ml of anhydrous heptane was added, drop by drop, to a stirred suspension formed by 7.85 g of commercial $LiAlH_4$ (207 mmoles) in 170 ml of anhydrous heptane, cooled at 0° C, the procedure being carried out under a nitrogen atmosphere. The whole was kept under stirring for some hours at the reflux temperature of the solvent, by controlling the N/Al ratio in solution up to an observed value of 1.

During the reaction, a development of $H_2$ was observed. At the end a filtration was performed and the product in solution was separated from the solvent by evaporating under vacuum at room temperature, dried ($5.10^{-3}$ mmHg, room temperature, 8 hours) and characterized.

14.5 g of a crystalline white solid were obtained having the following chemical analyses:

Found: Al% = 30.52; N% = 16.17; Li% = 0.003; $H_{active}$ = 12.03 meq/g. Calculated for $(HAl - NR)_n$: Al% = 31.70; N% = 16.46; Li% = $H_{active}$ = 11.76 meq/g.

The molecular weight, determined in boiling diethyl ether, was 400 according to the formation of a mixture of poly-N-alkyliminoalanes wherein the values of $n$ are 4 and 6 respectively, as also shown by other physical-chemical characterizations (RX difractometry, mass spectrometry, NMR). IR spectrum, in nujol, showed a $\nu$ Al—H band with a maximum at 1850 cm$^{-1}$ typical of an alane-derivative in which the aluminum atom is tetracoordinated.

EXAMPLE 2

7 g of commercial $LiAlH_4$ (184.5 mmoles) suspended in 200 ml of anhydrous benzene were reacted with 14 ml of iso $C_3H_7$ $NH_2$ (165 mmoles) in 35 ml of benzene according to the procedure of example 1. At the start the suspension was cooled to about 10° C. At the end, the product in solution, after filtration, was separated from the solvent by evaporating under vacuum at room temperature, dried ($5.10^{-3}$ mmHg, room temperature, 8 hours) and characterized.

13.5 g of a crystalline white solid were obtained having the following chemical analyses:

Found: Al% = 30.10; N% = 16.17; Li% = 0.001%; $H_{active}$ = 12.95 meq/g. Calculated for $(AlH-NR)_n$: Al% = 31.70; N% = 16.46; Li% = 0; $H_{active}$ = 11.76 meq/g.

The molecular weight, determined in boiling diethyl ether, was 400 according to the formation of a mixture of poly-N-alkyliminoalanes wherein the values of $n$ are 4 and 6 respectively, as shown by other physical-chemical characterizations (RX difractometry, mass spectrometry, NMR). IR Spectrum in nujol showed a $\nu$ 1—H band with a maximum at 1850 cm$^{-1}$, typical of an alane-derivative wherein the aluminum atom is tetracoordinated.

EXAMPLE 3

5.13 g of commercial $NaAlH_4$ (95 mmoles) suspended in 150 ml of anhydrous benzene were reacted with 7.5 ml of iso $C_3H_7NH_2$ (88.2 mmoles) in 50 ml of benzene according to the procedure of example 2. At the end the product in solution, after filtration, was separated from the solvent by evaporating under vacuum at room temperature, dried ($5.10^{-3}$ mmHg, room temperature, 8 hours) and characterized, 6.6 g of crystalline white solid were obtained having the following chemical analyses Found: Al% = 29.81; N% = 16.10; Na% = 0.3; $H_{active}$ = 11.2 meq/g. Calculated for $(AlH-NR)_n$: Al% = 31.70; N% = 16.46; Na% = 0; $H_{active}$ = 11.76 meq/g.

The molecular weight, determined in boiling diethyl ether, was 455, close to the theoretical value 510 calculated for an hexamer poly-N-alkyliminoalane, whose formation has been confirmed by various physical-chemical characterizations (RX difraction, mass spectrometry, NMR).

IR spectrum in nujol showed a $\nu$ Al-H band with a maximum at 1850 cm$^{-1}$, typical of an alane-derivative wherein the aluminum atom is tetracoordinated.

What we claim is:

1. A process of preparing a poly-N-alkyliminoalane containing repeated units represented by the formula

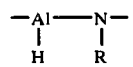

in which R is an aliphatic, cycloaliphatic or aromatic radical, which consists in reacting an alanate of an alkali or alkali-earth metal with a primary amine in the presence of a solvent selected from the aliphatic, cycloaliphatic and aromatic hydrocarbons, in an inert atmosphere, in the temperature range of from −20° to 250° C and in the pressure range of from atmospheric pressure to the vapor pressure of said solvent under the process conditions.

2. A process for the preparation of a poly-N-alkyliminoalane as claimed in claim 1 wherein said alanate is a member of the group consisting of $LiAlH_4$, $NaAlH_4$, $Li_3AlH_6$, $Na_3AlH_6$.

3. A process for the preparation of a poly-N-alkyliminoalane as claimed in claim 1 wherein said primary amine is a member of the group consisting of the primary aliphatic, cycloaliphatic and aromatic amines.

4. A process of preparing a poly-N-alkyliminoalane as claimed in claim 1, wherein R is an aliphatic radical.

5. A process of preparing a poly-N-alkyliminoalane as claimed in claim 4, wherein said primary amine is isopropylamine.

* * * * *

UNITED STATES PATENT AND TRADEMARK OFFICE
CERTIFICATE OF CORRECTION

PATENT NO. : 4,022,809
DATED : May 10, 1977
INVENTOR(S) : Salvatore Cucinella, et al It is certified that error appears in the above-identified patent and that said Letters Patent are hereby corrected as shown below:

Column 2, line 24, Before "-earth" correct "alkaline"

to read --alkali--.

line 28, Before "-earth" correct "alkaline"

to read --alkali--.

After line 40, correct first line of the formula to read --

$$MAlH_4 + H_2 NR \rightarrow \frac{1}{n} (AlHNR)_n + MH + 2H_2;$$

$$MH + Al + \frac{3}{2} H_2 \rightarrow MAlH_4 --.$$

Column 3, line 23, After "Li%=" insert --0--.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks